US00PP09862P

United States Patent [19]

Wambach et al.

[11] Patent Number: Plant 9,862

[45] Date of Patent: Apr. 22, 1997

[54] HYBRID TEA ROSE PLANT NAMED 'WAMSPER'

[75] Inventors: Catherine M. Wambach, Fredericksburg; Alex A. Wambach, deceased, late of Fredericksburg, both of Tex., by Catherine M. Wambach, Independent Executrix

[73] Assignee: Certified Roses, Inc., Tyler, Tex.

[21] Appl. No.: 579,124

[22] Filed: Dec. 27, 1995

[51] Int. Cl.[6] ..... A01H 5/00

[52] U.S. Cl. ..... Plt./20

[58] Field of Search ..... Plt./20, 21

*Primary Examiner*—Howard J. Locker

*Attorney, Agent, or Firm*—Christie, Parker & Hale, LLP

[57] ABSTRACT

A new hybrid tea rose plant producing red flowers.

1 Drawing Sheet

SUMMARY OF THE INVENTION

The present invention relates to a new and distinct variety of rose of the hybrid tea rose class which is the result of a cross of an undisseminated seedling, identified as 83-1, as seed parent and the rose known as 'First Prize' (U.S. Plant Pat. No. 2,774) as pollen parent. The varietal demonination of this new rose is 'Wamsper'.

Among the novel characteristics possessed by this new variety which distinguish it from its parents and all other varieties of which I am aware are its attractive red flowers that hold color well and to not "blue" upon aging.

Asexual reproduction by budding of the new variety as performed in Smith County, Tex. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

Parentage: Seedling '83-1'×'First Prize'.
Class: Hybrid tea.

The following is a detailed description of specimens of the new variety grown outdoors in Smith County, Tex. in the month of November. The color terminology used is in accordance with the Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:
- (1) *Size.*—Medium.
- (2) *Form.*—Ovoid.
- (3) *Color.*—When sepals first divide, bud color is near 59A.
- (4) *Sepals.*—Longer than bud, near 144B.
- (5) *Penduncle.*—Length: About 4 lcm. Aspect: Usually upright, numerous small prickles. Strength: Erect. Color: Near 144C.

B. Bloom:
- (1) *Size.*—Average size when fully expanded — about 9 cm.
- (2) *Borne.*—Singly, one to a stem.
- (3) *Form.*—High centered, some outer petals quill, inner petals roll under.
- (4) *Petalage.*—*Number of petals under normal conditions — about* 30.
- (5) *Color.*—⅓ to ½ open: top surface of outer and inner petals is near 46A; undersurface of outer and inner petals is near 53B; base of petals at point of attachment is near 20B and the general tonality from a distance is near 46A; a whitish longitudinal streak often appears on one of the outer petals. Fully open blooms: top surface of outer and inner petals is near 46A; undersurface of outer and inner petals is near 53B; base of petals at point of attachment is near 19B and the general tonality from a distance is near 46A. Upon aging, color of bloom lightens slightly with the petal top surface changing to lighter than near 46A and the petal undersurface to near 53B.
- (6) *Petal arrangement.*—Imbricated.
- (7) *Petaloids.*—Few, less than 10.
- (8) *Fragrance.*—Slight, spicy.
- (9) *Lasting quality.*—4–5 days as a cut flower.

C. Petals:
- (1) *Texture.*—Thick.
- (2) *Appearance.*—Velvety.
- (3) *Form.*—Ovoid.
- (4) *Persistence.*—Drop off cleanly.

REPRODUCTIVE ORGANS

A. Stamens:
- (1) *Arrangement.*—Irregularly arranged; stamens near 19B, anthers near 19B and filaments near 22B.
- (2) *Pollen.*—Color — near 23A.

B. Pistils:
- (1) *Styles.*—Bunched, medium length.
- (2) *Stigmas.*—Color — near 20C.

C. Characteristics of hips: Globular, average size, near 31A at maturity, seeds do not protrude.

PLANT

A. Form: Upright.

B. Growth. Vigorous, uniform branching; height attained about 5 feet at first season.

C. Foliage: Compound 3 and 5 leaflets.
- (1) *Size.*—Medium.
- (2) *Quantity.*—Abundant.

(3) *Color.*—New foliage: Upper side — near 59A. Underside — near 60B. Old Foliage: Upper side — near 147a. Underside — near 148B.
(4) *Shape.*—Elliptic.
(5) *Texture.*—Shiny upper surface; matte under surface.
(6) *Edge.*—Serrated.
(7) *Serration.*—Denticulate.
(8) *Leaf stem.*—Color — reddish green.
(9) *Stipules.*—Medium.
(10) *Resistance to disease*—Resistant to blackspot and mildew.

D. Wood:
(1) *New wood.*—Color — new shoots, reddish brown. Bark — smooth.

(2) *Old wood.*—Color — near 174C. Bark — smooth.

E. Flower stem: About 60 cm from last cut.

F. Thorns:
(1) *Thorns.*—Quantity (main stalk) — ordinary. On laterals from stalk — average. Form — curved downward, oval base. Length — medium. Color — near 182B when young. Position — irregular.
(2) *Prickles.*—Some.

G. Winter hardiness: Needs protection in winter climates.

It is claimed:

1. A new and distinct variety of rose plant of the hybrid tea rose class, substantially as shown and described.

* * * * *

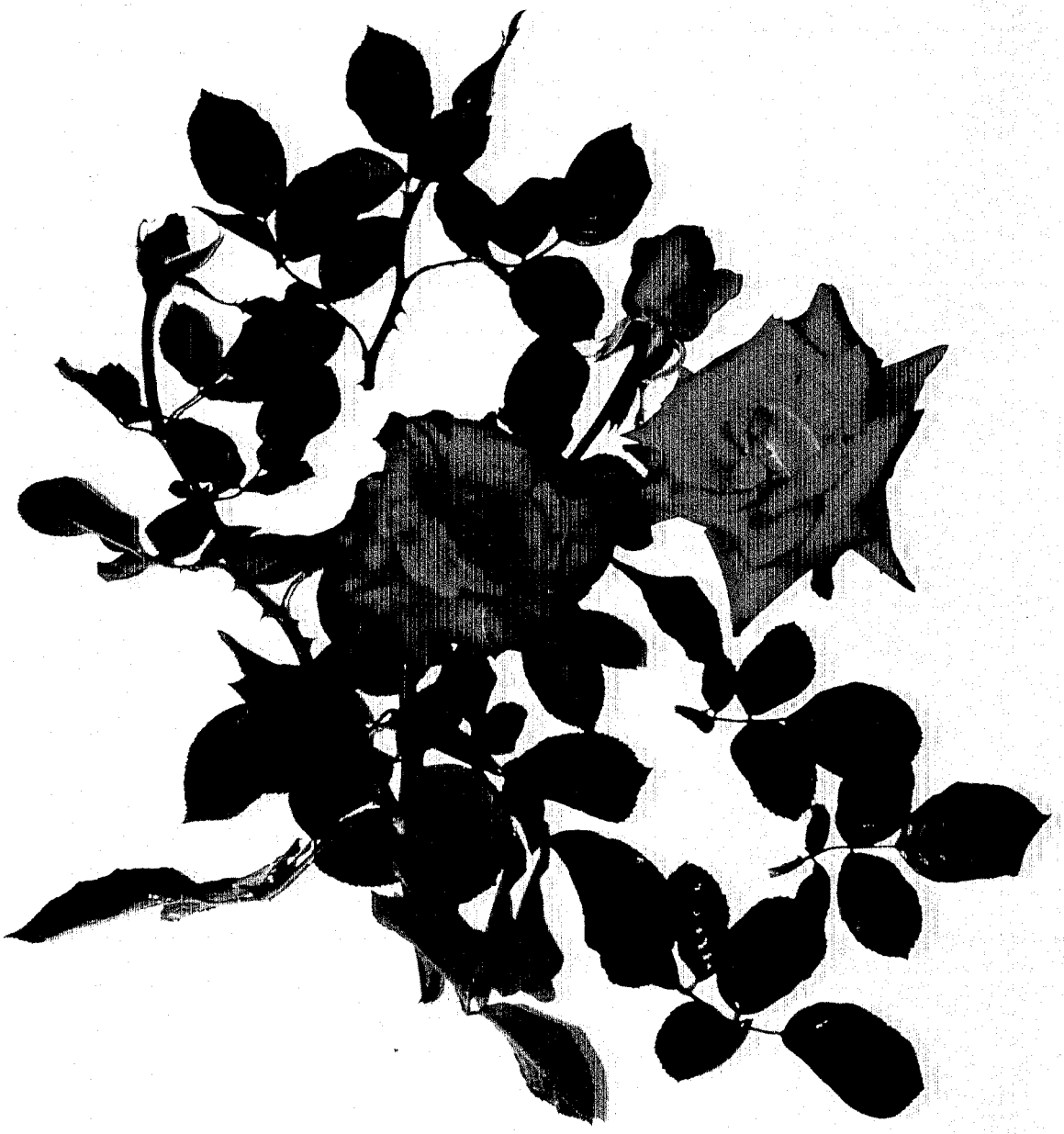

UNITED STATES PATENT AND TRADEMARK OFFICE

CERTIFICATE OF CORRECTION

PATENT NO. : Plant 9,862

DATED : April 22, 1997

INVENTOR(S) : Catherine M. Wambach; Alex A. Wambach

It is certified that error appears in the above-indentified patent and that said Letters Patent is hereby corrected as shown below:

Column 1, line 49, change "4 lcm." to -- 4 cm. --.

Signed and Sealed this

Twenty-third Day of December, 1997

*Attest:*

Bruce Lehman

BRUCE LEHMAN

*Attesting Officer*

*Commissioner of Patents and Trademarks*